United States Patent [19]

Tyler et al.

[11] Patent Number: 5,634,462
[45] Date of Patent: Jun. 3, 1997

[54] CORRUGATED INTER-FASCICULAR NERVE CUFF METHOD AND APPARATUS

[75] Inventors: Dustin J. Tyler, Westlake; Dominique M. Durand, Solon, both of Ohio

[73] Assignee: Case Western Reserve University, Cleveland, Ohio

[21] Appl. No.: 411,438

[22] Filed: Mar. 27, 1995

Related U.S. Application Data

[63] Continuation-in-part of Ser. No. 138,237, Oct. 15, 1993, Pat. No. 5,400,784.

[51] Int. Cl.$^6$ ............................... A61B 5/04; A61N 1/05
[52] U.S. Cl. ............................................. 128/642; 607/118
[58] Field of Search ................................. 128/642, 644; 607/117, 118

[56] References Cited

U.S. PATENT DOCUMENTS

| | | |
|---|---|---|
| 4,590,946 | 5/1986 | Loeb . |
| 4,602,624 | 7/1986 | Naples et al. . |
| 4,608,985 | 9/1986 | Crish et al. . |
| 4,623,355 | 11/1986 | Sawruk . |
| 4,628,942 | 12/1986 | Sweeney et al. . |
| 4,649,936 | 3/1987 | Ungar et al. . |
| 4,830,008 | 5/1989 | Meer . |
| 4,979,511 | 12/1990 | Terry, Jr. . |
| 5,282,468 | 2/1994 | Klepinski . |
| 5,400,784 | 3/1995 | Durand et al. ......................... 128/642 |

FOREIGN PATENT DOCUMENTS 509689  10/1992  European Pat. Off. ............... 128/644

OTHER PUBLICATIONS

Gregory G. Naples, et al. "A Spiral Nerve Cuff Electrode for Peripheral Nerve Stimulation", *IEEE Transactions on BioMed. Eng.*, vol. 35, No. 11, Nov. 1988.

William F. Agnew, et al. "Effects on Prolonged Electrical Stimulation of Peripheral Nerve", Chapter 6, pp. 142–167.

Gregory T.A. Kovacs, et al. "Regeneration Microelectrode Array for Peripheral Nerve Recording and Stimulation", *IEEE Transactions on BioMed. Eng.*, vol. 39, No. 9, Sep. 1992, pp. 893–902.

Robert M. Bradley, et al. "Functional Regeneration of Glossopharyngeal Nerve Through Micromachined Sieve Electrode Arrays", *Elsevier Scient Publishers*, pp. 84–90.

Wim L.C. Rutten, et al. "Sensitivity and Selectivity of Intraneural Stimulation Using a Silicon Electrode Array", *IEEE Transactions on BioMed. Eng.*, vol. 38, No. 2, Feb. 1991, pp. 192–198.

Nicola Nannini, et al., "Muscle Recruitment with Intrafascicular Electrodes", *IEEE Transactions on BioMed. Eng.*, vol. 38, No. 8, Aug. 1991, pp. 769–776.

Michael J. Decker, et al. "Functional Electrical Stimulation and Respiration During Sleep", 1993, American Physiological Society, pp. 1053–1061.

(List continued on next page.)

*Primary Examiner*—Lee S. Cohen
*Attorney, Agent, or Firm*—Fay, Sharpe, Beall, Fagan, Minnich & McKee

[57] ABSTRACT

A corrugated sheet of non-conductive biocompatible material is biased to circumferentially contract around a nerve or other body tissue. Conductive members are disposed on inwardly projecting portions of the corrugated sheet formed into a cylinder around the nerve. The conductive segments are electrically conductive for applying or recording electrical impulses or fluid conductive for infusing medications or draining fluids from the nerve. The corrugated sheet, when wrapped around a nerve, is self-biased to slowly controllably contract to its original size. Over a period of a few days, electrodes disposed on the sheet corrugations become embedded in the nerve without damage to the perineurium membrane surrounding the nerve axons. The electrodes and corrugations displace the fascicles of the nerve rather than damaging them by piercing the perineurium membrane. The epineurium membrane is initially pierced but rejuvinates around the contracted nerve cuff over time.

37 Claims, 6 Drawing Sheets

OTHER PUBLICATIONS

Lee C. Edmonds, et al. "The Effects of Transcutaneous Electrical Stimulation During Wakefulness and Sleep In Patients with Obstructive Sleep Apnea", pp. 1030–1036.

Hiroshi Miki, et al. "Effects of Electrical Stimulation of the Genioglossus on Upper Airway Resistance in Anesthetized Dogs", pp. 1279–1284.

Alan R. Schwartz, et al. "Effects of Electrical Stimulation of the Hypoglossal Nerve on Airflow Mechanics in the Isolated Upper Airway", *American Review of Respiratory Disease*, vol. 147, pp. 1144–1150, 1993.

B. Hillarp, et al. "Videoradiography at Submental Electrical Stimulation During Apnea in Obstructive Sleep Apnea Syndrome", Acta Radiologica 32 (1991) Fasc. 3, pp. 256–259.

Hiroshi Miki, et al. "Effects of Submental Electrical Stimulation During Sleep on Upper Airway Patency in Patients with Obstrcutive Sleep Apnea", pp. 1285–1289.

David W. Fairbanks, et al. "Neurostimulation for Obstructive Sleep Apnea: Investigations", *ENT Journal*, Jan. 1993.

CORRUGATED INTER-FASCICULAR NERVE CUFF METHOD AND APPARATUS

CROSS-REFERENCE TO RELATED APPLICATIONS

This is a continuation-in-part of application Ser. No. 08/138,237, filed Oct. 15, 1993, now U.S. Pat. No. 5,400,784.

BACKGROUND OF THE INVENTION

The present invention relates to the biomedical arts, particularly implantable nerve cuffs for both stimulating and monitoring nerve activity. The present invention finds application in electrodes embedded in nerve trunks or other small tissue strands and will be described with reference thereto. It is to be appreciated, however, that the invention is also applicable to medicinal infusers and other implanted biomedical devices for introducing, monitoring, or removing matter, fluids, or energy.

Functional electrical stimulation of the nervous system has been shown in recent years to offer great hope in restoring some degree of lost sensory and motor function in stroke victims and individuals with spinal cord lesions. In certain specialized applications, such as in the treatment of sleep apnea syndrome, it is necessary to simultaneously monitor as well as generate electrical signals in nerves. A generic sensor/effector electrode is suggested in U.S. Pat. No. 4,830,008 to Meer. That patent, however, provides no specific details regarding the electrode.

Methods and apparatus in which functional electrical stimulation and/or recording are utilized to restore a particular function broadly include:

(1) the use of surface electrodes to activate nerves in a general region of interest;
(2) the use of intramuscular electrodes, also to activate nerves in a general region;
(3) the use of nerve cuff electrodes placed around specific nerves of interest and used to activate individual nerves specifically; and,
(4) the use of regeneration-type neural interfaces including microelectrode arrays.

The third alternative, i.e. cuff electrodes, offers advantages over the first two in that it requires the least amount of stimulating current to produce a desired effect and hence injects the least amount of charge into the tissue itself. Because the use of nerve cuff electrodes requires delicate surgery and may damage the nerves, they are usually contemplated only when excitation of specific, isolated muscles is desired, or when unidirectional propagation action potentials are required.

The prior art cuff electrodes can be generally classified as split-cylinder type or self-curling coil type. The split-cylinder type cuff electrode typically includes a cylinder of dielectric material defining a bore therethrough having sufficient diameter to receive a nerve trunk to be electrically stimulated. Two or three annular electrodes are positioned on the inner surface of the bore for applying an electrical stimuli. The electrical stimuli, for example, may be used to provide functional electrical stimulation, to block neural nerve impulses traveling along the nerve trunk, or to cause other effects.

Examples of cylindrical type cuff electrodes and their use include U.S. Pat. Nos. 4,608,985, 4,628,942 and 4,649,936, all assigned to the assignee of the instant application.

The self-curling type prior art cuff electrodes typically include a self-curling sheet of non-conductive material biased to curl into a tight spiral. A pair of conductive strips are disposed on the self-curling sheet extending peripherally around the diameter of cuff passage. The conductive segments may be electrically conductive for applying electrical impulses or fluid conductive for infusing or extracting medications. An example of this type cuff electrode is U.S. Pat. No. 4,602,624, assigned to the assignee of the instant application.

In use, a first edge of the self-curling sheet is disposed adjacent a nerve trunk which is to receive the cuff therearound. The self-curling sheet is permitted to curl around the nerve forming an annular cuff. The effectiveness of this type of cuff is limited, however, due to the placement of the conductive material on the nerve surface, rather than placement within the interior portions of the nerve. Also, although presenting an improvement over the split cylinder cuff electrode type described above, the self-curling type electrodes tend to interfere with normal swelling and movement of the nerve. Damage to the nerve fibers can result when the self-curling cuff lodges too tight around the nerve preventing nutrients, blood and other critical fluid flow.

Another prior art approach to electrical stimulation of the nervous system is taught by Nannini, et al. in *Muscle Recruitment with Intrafascicular Electrodes*, I.E.E.E. Transactions on Biomedical Engineering, Vol. 38, No. 8, August 1991. There, a bipolar, intrafascicular electrode is used to penetrate the perineurium membrane and is advanced into an individual fascicle of a nerve. A bipolar electrode pair is formed on two small insulated wires. A Tungsten needle is then used to thread a first (inside) wire of the electrode through the nerve fascicle for about 1 cm. with an exposed tip portion of the wire entering this region. The second (outside) wire is not threaded through the nerve but is placed on the outside of the fascicle. The distal ends of the two wires are fastened to the fascicular endoneurium with a suture. The proximal end is secured in place by suturing a loop emerging from a piece of silastic tubing to the epineurium. The tubing is led to the skin and the wound is closed, leaving the two wires accessible. Although this method is highly invasive and can permanently damage the nerve through penetration of the perineurium, it demonstrates the advantages, e.g. effectiveness, of intra-fascicular recording and stimulating electrodes.

Regeneration-type neural interfaces have been used as another form of recording and stimulating electrical activity from within a nerve. One example is U.S. Pat. No. 4,623,355 to Sawruk. The basic idea behind this type of interface is to manufacture a thin diaphragm with many small holes that can be positioned between the cut ends of a peripheral nerve. The nerve is left to regenerate over time through the many small holes in the diaphragm. The holes are formed by mechanical or laser drilling, or by semiconductor fabrication techniques including wet and dry etching of silicon substrates. Sophisticated interfaces include active electronics on the devices. However, although these devices are theoretically attractive, actual functionality falls short primarily because the nerves tend to regenerate around the interface rather than through it.

Our earlier co-pending application Ser. No. 08/138,237, filed Oct. 15, 1993 teaches a slowly penetrating interfascicular nerve cuff electrode which includes a split cylinder cuff embodiment arranged with "frayed" ends formed from non-conductive surgical tube material. The ends comprise a plurality of spring members formed by longitudinal slices into the ends of the cylinder. Each of the plurality of spring members carries at least one fin member construction which in turn supports at least one medication or electrical energy conductive member. Each of the spring members are self-biased to slowly drivingly urge the fin members into the nerve trunk or other body tissue at a predetermined rate. The conductive members carried on the fin members are thus correspondingly driven into the nerve tissue. The predetermined driving rate as well as the shape of the fins are particularly selected to be slow enough and blunt enough, respectively, so that the axons within the nerve trunk are displaced rather than destroyed or pierced by the at least one medication or electrical energy conductive member. Although the inner diameter of the cuff embodiments of our earlier patent are necessarily slightly greater than the outer diameter of the target tissue, it would be desirable to provide additional circumferential elasticity for anticipated excessive swelling beyond the limits of the cuff inner diameter boundary. A direct advantage to providing additional circumferential elasticity in the cuff, as an alternative to providing a gap or space to accommodate the swelling, is an increased effectiveness of the cuff.

SUMMARY OF THE INVENTION

The present invention contemplates new and improved cuff electrodes which combine the best features of the above interfascicular and cuff type prior art methodologies in novel ways. The improved cuffs of the present invention are readily installed without damaging the nerve trunk or other surrounding tissue and are adapted to circumferentially expand and contract in correspondence with tissue swelling and movement, and to minimize contact between the cuff and the nerve or tissue surrounding the nerve. Further, the present invention contemplates use of the novel cuff electrodes in the treatment of sleep apnea syndrome.

In accordance with the present invention, a corrugated substantially cylindrical cuff is provided for encircling a nerve trunk or other body tissue with at least one medication and/or electrical energy conductive member.

A first embodiment of the preferred cuff includes a corrugated non-conductive sheet having a plurality of conductive members disposed on a first side of the sheet. The non-conductive sheet is adapted to be wrapped around a nerve or other body tissue with the first side of the sheet engaging the nerve or body tissue. The cuff is molded to include a plurality of longitudinally extending, spaced apart corrugations defined by a plurality of rounded folds or alternating series of furrows and ridges. The alternating furrows and ridges are evenly distributed over the cuff body in a direction transverse the longitudinal direction. Further, the corrugations define an inherent transverse elasticity in the cuff which, when wrapped around a nerve, provides circumferential expandability and contractibility. Further, the corrugations minimize the contact between the cuff and the nerve or tissue surrounding the nerve. The transverse dimension of the cuff body is selected to be slightly smaller than the circumference of the target nerve or tissue. The cuff body is resiliently extended or stretched around the nerve whereupon the cuff ends are connected together. Preferably, each of the plurality of corrugations carries at least one medication or electrical energy conductive member. Overall, the cuff is self-biased to slowly drivingly urge each of the plurality of corrugations carrying conductive portions directly to the nerve trunk or other body tissue. The rounded folds are adapted to be able to pierce the epineurium membrane while avoiding piercing the perineurium membrane.

Control over the spring constant or throttling force exerted by the cuff corrugations on the target tissue is accomplished through a selection of a specific non-conductive material type and by controlling the thickness comprising the cylindrical body itself and the thickness, size and dimensions of the plurality of corrugations forming the cylindrical body. Using these parameters the cuff can be configured to rest on the surface tissue and not to penetrate the epineurium membrane.

Another embodiment of the cuff includes a corrugated non-conductive sheet having a plurality of conductive members disposed on a first side of the sheet. The corrugations are defined by a plurality of sharp creases or repeated series of vee folds. The non-conductive sheet is adapted to be wrapped around a nerve or other body tissue with the first side of the sheet engaging the nerve or body tissue. The repeated series of vee folds extend longitudinally over the cuff and are disposed on the non-conductive sheet in a manner that they extend radially inwardly to the nerve or other target body tissue when the cuff is wrapped therearound. The plurality of creases or series of vee folds provide an inherent transverse elasticity in the cuff, which is defined by the size, number, thickness and overall crease or corrugation configuration and minimizes the contact between the cuff and nerve or tissue surrounding the nerve. When wrapped around a nerve, the cuff elasticity provides for circumferential expansion and contraction. Further, the pointed ridges of the vee folds are particularly well-suited for piercing the epineurium membrane of a nerve while avoiding piercing a perineurium membrane of the nerve, as well as resting on the surface tissue.

A third embodiment of the instant cuff includes a corrugated non-conductive sheet having a plurality of conductive members disposed on a first side of the sheet. A plurality of longitudinally extending fin members are connected to a corresponding plurality of alternate peaks and valleys of the corrugations. The non-conductive sheet is adapted to be wrapped around a nerve or other body tissue in a manner that the plurality of longitudinally extending fin members extend radially inwardly toward the longitudinal axial center of the nerve over which the cuff is wrapped. A plurality of conductive members are disposed on selected ones of the plurality of fin members and on selected ones of the peaks and valleys for engaging the target nerve or other body tissue. Each of the plurality of fin members are adapted for piercing the epineurium membrane of a nerve while avoiding piercing the perineurium membrane of the nerve, or alternatively for resting on the surface tissue.

A primary advantage of the present invention is that it is easily installed on a nerve while providing improved intimate electromechanical contact between the individual axons in the nerve bundle and at least one medication or electrical energy conductive member. Another advantage of the present invention is that the axons and perineurium membrane within the nerve trunk remain intact through the careful selection of the circumferential elasticity of the corrugated cuff and the slow rate of circumferential contraction and corresponding radial penetrating motion of the self-embedding cuff members.

Still another advantage of the present invention is that a plurality of medication or electrical energy conductive members are capable of individually selectively communicating respective medication or electrical energy quantities to the nerve trunk at different rates and quantities.

Yet another advantage of the present invention is that the various embodiments are not sensitive to variations such as expansion of the diameter of the nerve tissue due to swelling or differences between tissue size from one patient to another.

Still further advantages of the present invention will become apparent to those of ordinary skill in the art upon reading and understanding the following detailed description of the preferred embodiments.

BRIEF DESCRIPTION OF THE DRAWINGS

The invention may take form in various parts and arrangements of parts or in various steps and arrangements of steps. The Figures and the described structure and methods are only for purposes of illustrating the preferred embodiments of the invention and are not to be construed as limiting same.

DETAILED DESCRIPTION OF THE PREFERRED AND ALTERNATIVE EMBODIMENTS

Figure 1:
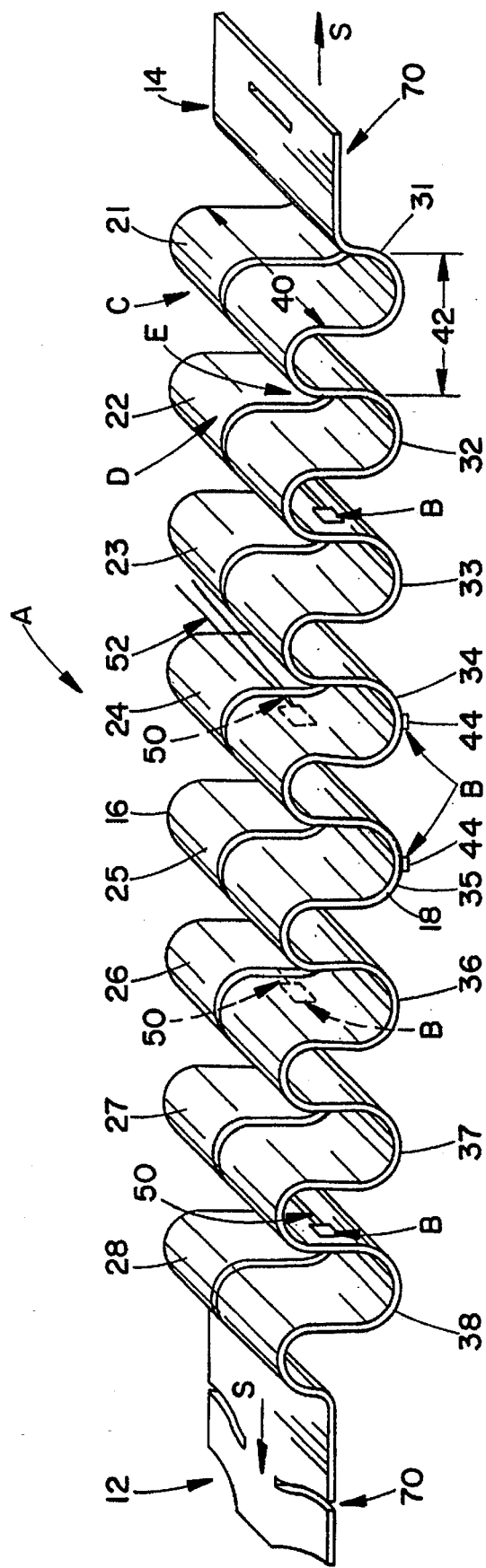
FIG. 1 is a perspective view of a corrugated cylindrical cuff in accordance with the preferred embodiment of the present invention illustrated in a generally flat, uncurled configuration.
Figure 2:
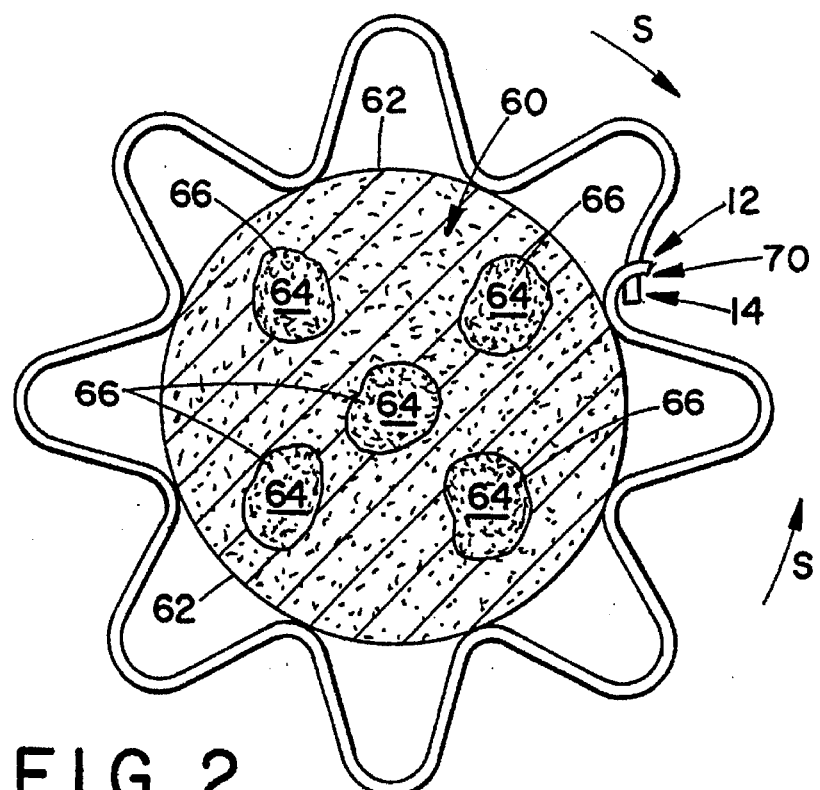
FIG. 2 is a sectional end view of the corrugated cylindrical cuff of FIG. 1 in a curled and circumferentially expanded state installed around a body tissue fiber.
Figure 3:
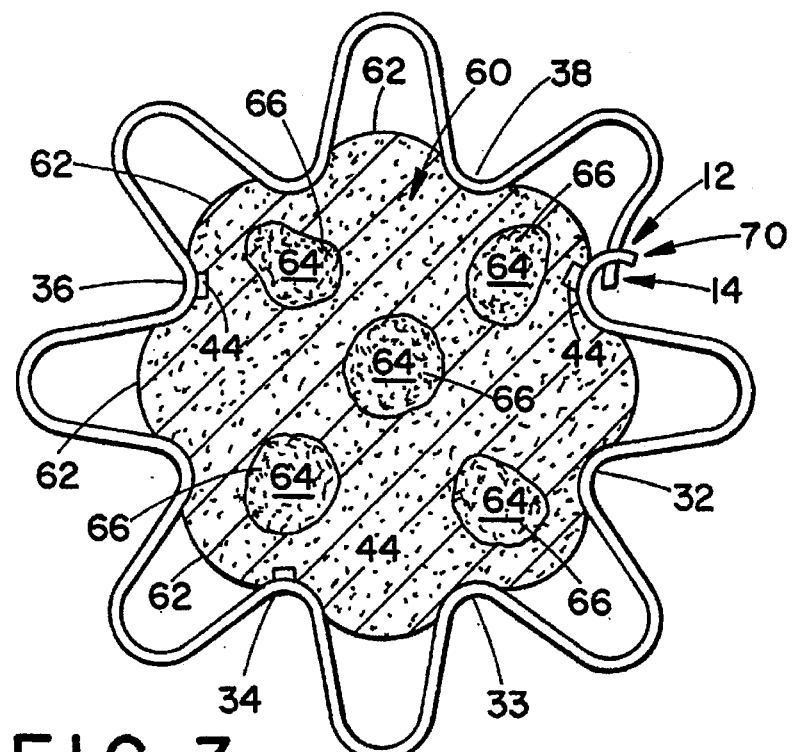
FIG. 3 is a sectional end view of the corrugated cylindrical cuff of FIG. 2 installed over the body tissue fiber in an embedded circumferentially contracted and relaxed condition.
Figure 4:
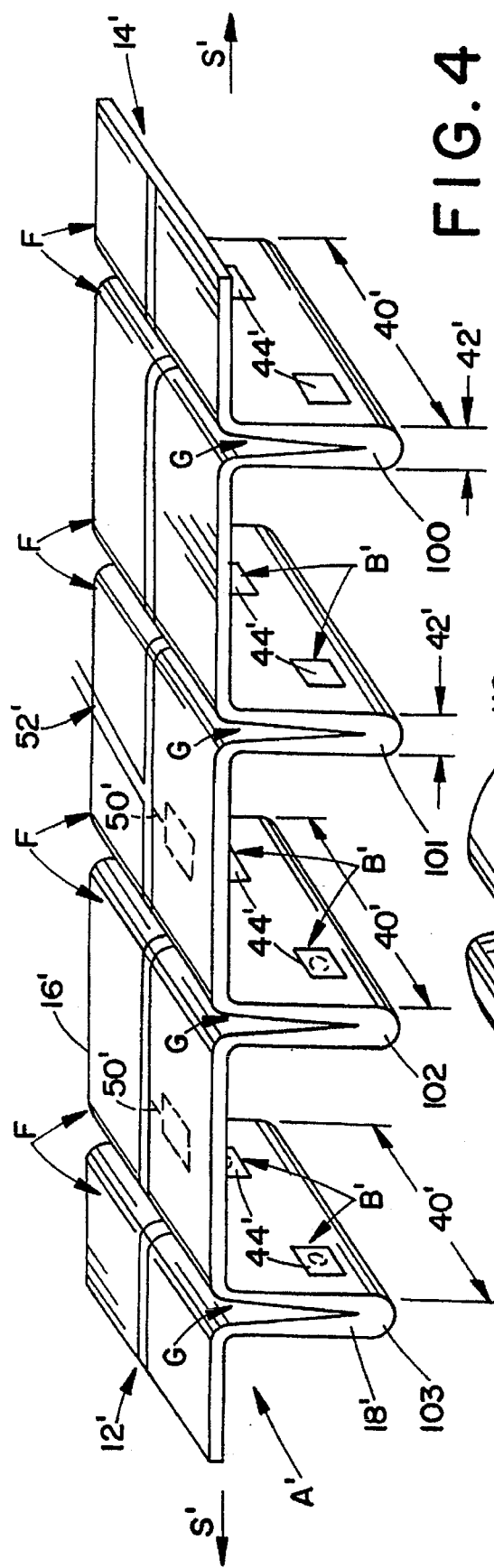
FIG. 4 is a perspective view of a corrugated cylindrical cuff in accordance with a second preferred embodiment of the present invention illustrated in a generally flat, uncurled configuration.
Figure 5:
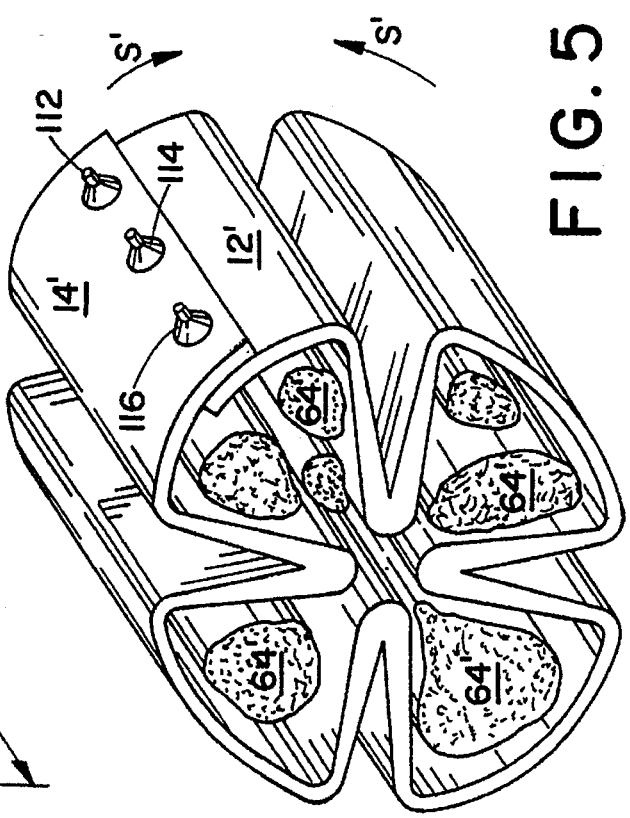
FIG. 5 is a sectional end view of the corrugated cylindrical cuff of FIG. 4 installed over a body tissue fiber in an embedded circumferentially contracted and relaxed condition.
Figure 6:
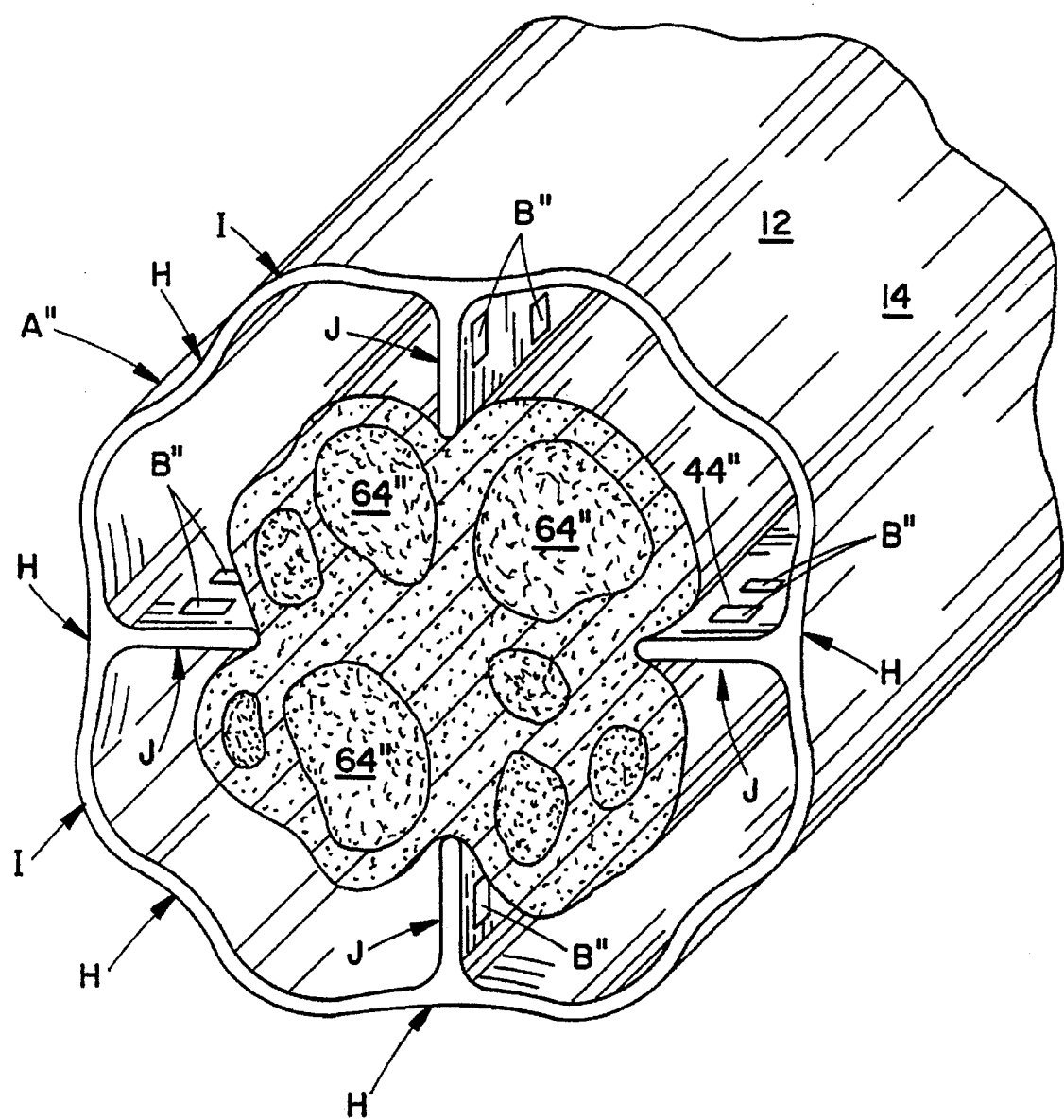
FIG. 6 is a perspective end view of a corrugated cylindrical cuff according to a third preferred embodiment installed over a body tissue fiber in a partially embedded and partially circumferential y contracted condition.

The first preferred embodiment of the invention is shown in FIGS. 1-3 of the drawings, the second preferred embodiment in FIGS. 4 and 5 and a third preferred embodiment in FIG. 6. For ease of illustration and discussion, like elements will be referred to by like numerals with a primed (') suffix and new elements will be referred to by new numerals.

With reference first to FIGS. 1-3, an implantable cuff for encircling a nerve or other tissue includes a corrugated non-conductive resilient sheet A upon which one or more conductive segments B are attached or embedded. The segments B are preferably electrically conductive but may also be chemical, medication, or otherwise fluid conductive as well as any combination of the above. The corrugated sheet A is illustrated in an open or unrolled position for the sake of illustration and is preferably molded from silastic but may be made from other suitable resilient flexible materials such as those typically used in the manufacture of non-conductive biocompatible surgical tubing.

The preferred corrugated sheet A includes a plurality of longitudinally spaced apart undulations C formed in the sheet over its entire length. The undulations C define an alternating pattern of peaks D and valleys E in the corrugated sheet A. The sheet A is resiliently biased to spring back to its original molded shape and is thus adapted for longitudinal expanding and contracting when suitable forces are applied. Accordingly, when the cuff is applied to a nerve or other body tissue, the cuff readily expands and contracts commensurate with the body tissue or nerve growth to prevent and forestall damage thereto.

With continued reference to FIGS. 1-3 but with particular attention to FIG. 1, the sheet A is preferably formed of a single layer of flexible rubberized biocompatible material. However, it may also be formed by laminating two or more materials for added strength or to realize other characteristics in the final cuff device. The sheet may include a first and oppositely disposed second generally planar surface biased in the manner set forth in our earlier patent referenced above, to cause the sheet to curl into a closed cylinder. In the preferred embodiment, however, the sheet A is a generally planar rectangle which extends from a first end 12 to an oppositely disposed second end 14 and from a first or arresting edge 16 to an oppositely disposed second or escape edge 18.

A plurality of alternate furrows 21–28 and ridges 31–38 are evenly distributed over the sheet A. Each of the alternate furrows 21–28 and ridges 31–38 has a longitudinal or first dimension 40, generally parallel to the first and second ends 12, 14. The alternate furrows and ridges further include a transverse or a second dimension 42, generally parallel to the first and second edges 16, 18. In the preferred embodiment, the alternate furrows and ridges are evenly distributed over the entire corrugated sheet A. However, it is to be understood that alterations to the preferred cuff are possible including the modification of limiting the number of corrugations to a single furrow, e.g. 22, or a single ridge, e.g. 33 or to any combination of furrows and ridges. Also, in this and the other preferred embodiments described below, the longitudinal orientation of the corrugations may be altered to be slightly off parallel with the first and second ends 12, 14. More particularly, it is contemplated within the scope of the instant invention to provide a cuff having spiral or helical corrugations or combinations of longitudinal and spiral corrugated portions.

As illustrated in the Figures, each of the alternate furrows and ridges have a plurality of conductive segments B received thereon. Each of the conductive segments B are preferably molded within the sheet A during the initial phase of manufacture. Later, after molding and curing where necessary, portions of the sheet immediately adjacent the conductive segments B are trimmed away exposing the conductive segments B individually.

In the preferred embodiment illustrated, the segments B are electrically conductive electrodes 44. However, through simple modification of the structure of the electrodes 44, such as by forming fluid conduits or ducts, the elements are adaptable to become medication or fluid conductive. In addition, a selected one or more of the conductive segments may be adapted to be medication conductive while the other segments adapted to remain electrically conductive for a combined chemical and electrical stimulation. Further, chemical and electrical conduction is not constrained to flow only into the nerve from the cuff. Rather, the chemical and electrical conductive elements are adapted to conduct chemicals and electricity both from the cuff to the nerve and into the cuff from the nerve for stimulating and monitoring various nerve properties, activities, and characteristics, respectively. Accordingly, the cuff is also useful in such applications as treatment of sleep apnea where combined sensor/effector cuff electrodes are required. U.S. Pat. No. 4,830,008 to Meer, incorporated herein by reference, describes a preferred method and generic apparatus for treating sleep apnea. The present invention extends the preferred cuff embodiments to the Meer teachings.

With further continued reference to FIGS. 1–3, each of the plurality of electrodes 44 are individually connected to an operatively associated electrical signal generating a source (not shown) or electrical signal monitoring device (not shown) through individual fine conductive wires. In the FIGURES, the fine conductive wires are illustrated as a plurality of individual conductors 50 which extend longitudinally from the conductive segments B to a location between the first edge 16 and the second edge 18 of the implantable cuff. From that point, the plurality of conductors 50 extend circumferentially around the implantable cuff to a common exit area 52. There, the plurality of conductors 50 extend away from the nerve encircled by the implantable cuff for subsequent attachment to the operatively associated electrical signal or monitoring device(s). In the preferred embodiment, the plurality of conductors 50 extend from the conductive segments B completely embedded in the non-conductive material comprising the sheet A. In this way, they are insulated from direct contact with either the nerve, other conductors, or other surrounding tissue. Also, the non-conductive sheet A affords a level of structural integrity to the somewhat otherwise frail conductors.

Although the preferred embodiment includes electrically conductive segments B having one or more discrete electrodes disposed thereat, one alternative includes forming a micro-multielectrode array in silicon using semiconductor fabrication technology. An example of this approach is set forth in Wim L. C. Rutten, Harmen J. Van Wier and Johan H. M. Put, "Sensitivity and Selectivity of Intraneural Stimulation Using a Silicon Electrode Array", *IEEE Trans. Biomed., eng.* Vol. 38, pp. 192–198, February 1991. Using this and similar technologies currently available including micro-lithography and micro-integrated electronics, the plurality of conductors may be formed on fine flexible silicon substrates. In this way, active and intelligent electronics may be included on the cuff apparatus itself.

In use, the implantable cuff is laid substantially flat manually and maintained in the position illustrated in FIG. 1. Next, the cuff is aligned with, positioned, and stretched over a target nerve 60 (FIGS. 2 and 3). The cuff is stretched in a direction marked in the figures as S to completely encircle the nerve at which point the overlapping ends 12, 14 are connected together. Preferably, a manually operated connector arrangement such as an arrowhead connector 70 is used to join the ends 12, 4.

Figure 7A:
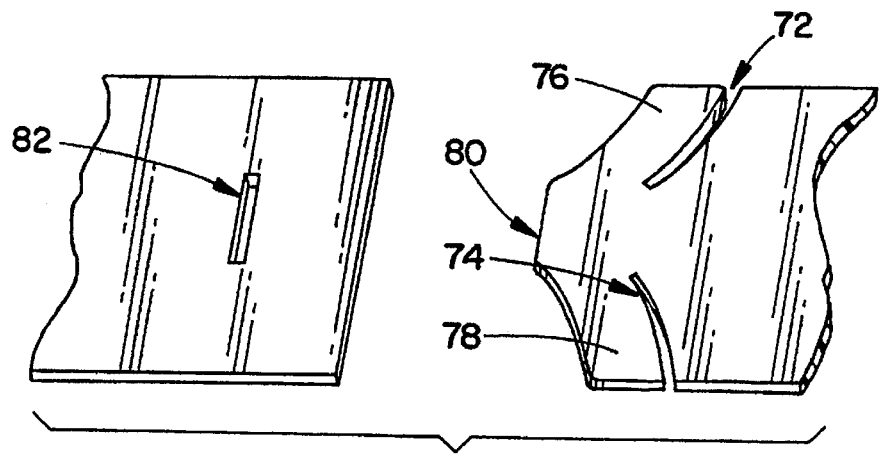
FIGS. 7a, 7b and 7c illustrate the preferred method and apparatus for connecting the ends of the corrugated cuff electrode during installation of same; and, FIGS. 8a, 8b and 8c illustrate a second preferred method and apparatus for connecting the ends of the corrugated cuff electrode for installation.
Figure 7B:
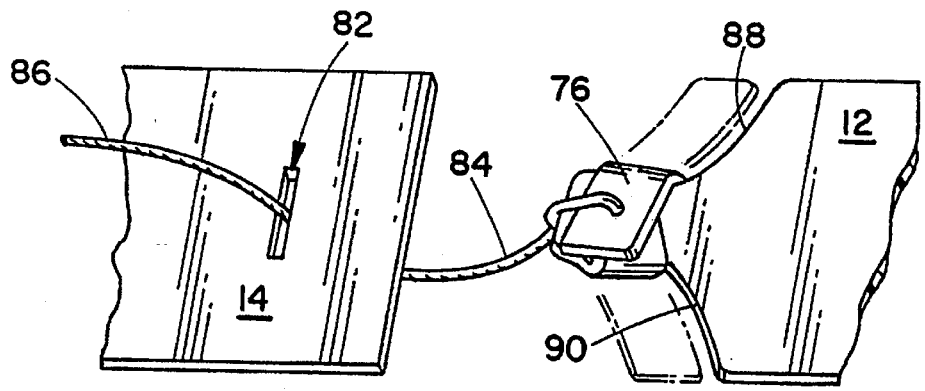
Figure 7C:
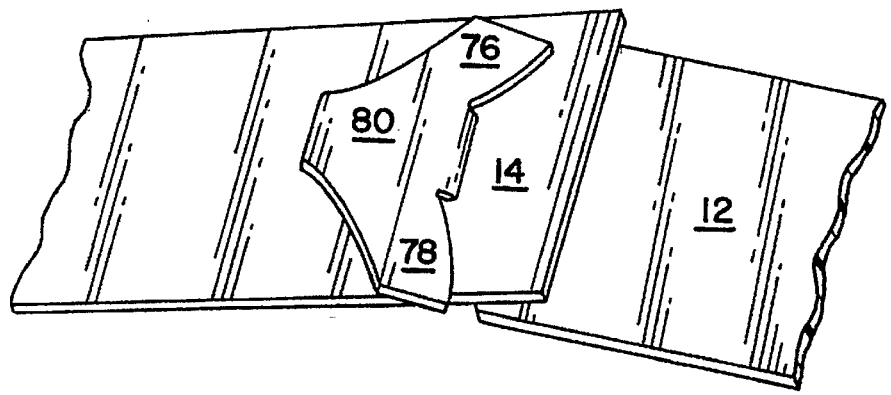

FIGS. 7a–7c best illustrate the arrowhead connector 70 according to the present invention. The first end 12 of the sheet A includes a pair of cut out regions 72, 74 which defined a corresponding pair of tabs or barbed ears 76, 78. Also, in order to best facilitate connecting ends 12, 14, the first end 12 is adapted to form a pointed nose 80 for engaging and piloting the first end 12 through a corresponding slot 82 defined in the second end 14. A suitable suture 84 is preferably used to maintain the first and second ears 76, 78 in a folded-over orientation best illustrated in FIG. 7b. A free end 86 of the suture is advanced through the slot 82. Next, the pair of ears 76, 78 are pulled through the slot 82 until edges 88, 90 defined by the pair of cut out regions 72, 74 on the first end 12 engage the second end 14 of the cuff. In this position, the suture 84 is trimmed away permitting the pair of ears 76, 78 to unfurrow, or spring open locking the ends 12, 14 together, illustrated best in FIG. 7C. Although the preferred arrowhead connector 70 is illustrated as being formed of the same material as the sheet A, it is possible to bond connectors of other materials to opposite ends of the sheet. As an example, the arrowhead connector may be made of biocompatible plastic glued or attached to the first end 12.

FIGS. 2 and 3 illustrate the corrugated cylindrical nerve cuff electrode of the first preferred embodiment in an initial (FIG. 2) stretched state and in a final (FIG. 3) relaxed state applied on a nerve. In general, the nerve 60 is surrounded by a loose membrane called the epineurium membrane 62. The nerve is typically organized into several groups of axons called fascicles 64. Each fascicle 64 is surrounded by a membrane called the perineurium membrane 66. In this embodiment, the corrugated nerve cuff slowly circumferentially contracts around the nerve, driving the plurality of ridges 31–38 through the epineurium membrane 62 and into the target nerve 60. This throttling type motion effectively inserts the conductive members B on the sheet A through the epineurium membrane 62 and into the nerve 60 without puncturing the perineurium membrane 66 of any of the fascicles 64 within the nerve. Instead, the fascicles 64 are displaced, rather than pierced. The epineurium membrane 62 is of course pierced at locations corresponding to the cuff corrugation ridges. The method of using this and the other preferred embodiments inserts electrodes into the nerve interfascicularly without penetration of the perineurium membrane. The corrugations are gently and slowly migrated into the nerve gradually over a period of time preferably long enough to minimize the pressure on the nerve. Typically, the time period required for the cuff to function properly extends from about one (1) hour to several days depending upon particular application and situation.

The driving force which motivates the conductive members B inward, however, is provided by the mechanical spring action of the undulations C. This unique design illustrated in the Figures allows the placement of the electrodes deep inside the nerves with minimal damage to the nerve itself. The electrodes 44 are each capable of activating separate and distinct regions within the nerve, along both the longitudinal and radial axis of the nerve, which was not previously accessible by other types of electrodes without the associated damage described in the background above. The electrodes are also capable of sensing small neural signals with better signal to noise ratios due to the close proximity of each of the electrodes to the axons comprising the fascicles.

It is to be appreciated that by controlling the spring constant or throttling force exerted by the cuff corrugations, the cuff can be configured to rest on a surface and not penetrate the epineurium membrane. FIG. 2 illustrates the cuff in this type of situation, with contact points 13 depicting a portion of the cuff resting on the surface. It is to be further understood that such surface implementation may be accomplished by all the remaining embodiments as well.

The second preferred embodiment of the corrugated nerve cuff is illustrated in FIGS. 4 and 5. With reference now to those Figures, a second preferred implantable cuff for encircling a nerve or other tissue includes a corrugated non-conductive resilient sheet A' upon which one or more conductive segments B' are attached or embedded. The segments B' are preferably electrically conductive but may also be chemically or fluid conductive as well as combinations of electrical and fluid conductive. The corrugated sheet A' is illustrated in an opened or unrolled position for the sake of illustration and is preferably molded from silastic but may be made from other suitable biocompatible resilient flexible materials such as those used in surgical tubing.

The corrugated sheet A' includes a plurality of sharp creases F formed in the sheet over its entire length. The sharp creases F define a repeated series of vee folds G in the corrugated sheet A'. As with the first embodiment, the instant sheet A' is resiliently biased to spring back to its original molded shape and is thus adapted for longitudinal expanding and contracting when suitable forces are applied. Accordingly, when the cuff is applied to a nerve or other body tissue such as shown in FIG. 5, the cuff readily expands and contracts commensurate with the body tissue movement or nerve swelling motion to prevent or forestall damage thereto.

With continued reference to FIGS. 4 and 5, the sheet A' is preferably formed of a single layer of flexible rubberized biocompatible material. However, the sheet may be laminated to form a self-curling cuff according to the teachings of our earlier co-pending application referenced above. In any case, the sheet A' is a generally planar rectangle which extends from a first end 12' to an oppositely disposed second end 14' and from a first or arresting edge 16' to an oppositely disposed second or escape edge 18'.

A plurality of peaks 100-103 are evenly distributed over the sheet A'. Each of the plurality of peaks 100-103 has a longitudinal or first dimension 40', generally parallel to the first and second ends 12', 14'. The peaks further include a transverse or second dimension 42', generally parallel to the first and second edges 16', 18'. In the instant embodiment, the plurality of peaks 100-103 are evenly distributed over the entire corrugated sheet A'. However, it is to be understood that the number and distribution of peaks may be modified to include a single peak, a number of peaks less than that illustrated, or a number of peaks greater than that illustrated.

A plurality of conductive segments B' are disposed on each of the plurality of peaks 100-103 and are preferably molded within the sheet A' during the initial phase of manufacture. Later, after molding and curing (where necessary), portions of the sheet immediately adjacent the conductive segments B' are trimmed away exposing the conductive segments B' individually.

In the second preferred embodiment illustrated, the segments B' are electrically conductive electrodes 44'. However, through simple modification of the structure of the electrodes 44', such as by forming fluid conduits or ducts, the elements are adaptable to become medication or fluid conducted. In addition, selected ones of the conductive segments may be adapted to be medication conductive while the other segments adapted to remain electrically conductive for a combined chemical and electrical stimulation or sampling. Further, chemical and electrical conduction is not constrained to flow only into the nerve from the cuff. Rather, the chemical and electrical conductive elements are adapted to conduct chemicals and electricity both from the cuff to the nerve and into the cuff from the nerve for stimulating and monitoring various nerve properties, activities, and characteristics, respectively. Accordingly, the cuff is particularly useful in such applications as treatment of sleep apnea where combined sensor/effector cuff electrodes are required. U.S. Pat. No. 4,830,008 to Meer, incorporated herein by reference, describes a preferred method and generic apparatus for treating sleep apnea. The present invention extends the preferred cuff embodiments to the Meer teachings.

With continued reference to FIGS. 4 and 5, each of the plurality of electrodes 44' are individually connected to an operatively associated external electrical signal generating source (not shown) or electrical signal monitoring device (not shown) through individual fine conductive wires. In the Figures, the conductive wires are illustrated as a plurality of individual conductors 50' which extend longitudinally from the conductive segments B' to a location between the first edge 16' and the second edge 18' of the implantable cuff. From that point, the plurality of conductors 50' extend circumferentially around the implantable cuff to a common exit area 52'. There, the plurality of conductors 50' extend away from the nerve encircled by the implantable cuff for subsequent attachment to the operatively associated external signal or monitoring device(s). Preferably, the plurality of conductors 50' are completely embedded in the non-conductive biocompatible material comprising the sheet A'. In this way, they are insulated from direct contact with other conductors and surrounding body tissue. Further, disposition of the wires in this manner affords added structural integrity to the otherwise frail conductors. As described in connection with the first preferred embodiment, the conductors and conductive segments may be provided using semiconductor fabrication technology.

In use, the implantable cuff is laid substantially flat manually and maintained in the position illustrated in FIG. 4. Next, the cuff is aligned with, positioned, and stretched over a target nerve 60'. The cuff is stretched in a direction marked in the Figures as S' to completely encircle the nerve at which point the overlapping ends 12', 14' are connected together. As an alternative to the arrowhead connector 70 illustrated in FIGURES 7a-7c, a rivet connector 110 is used to join the ends 12', 14'.

Figure 8A:
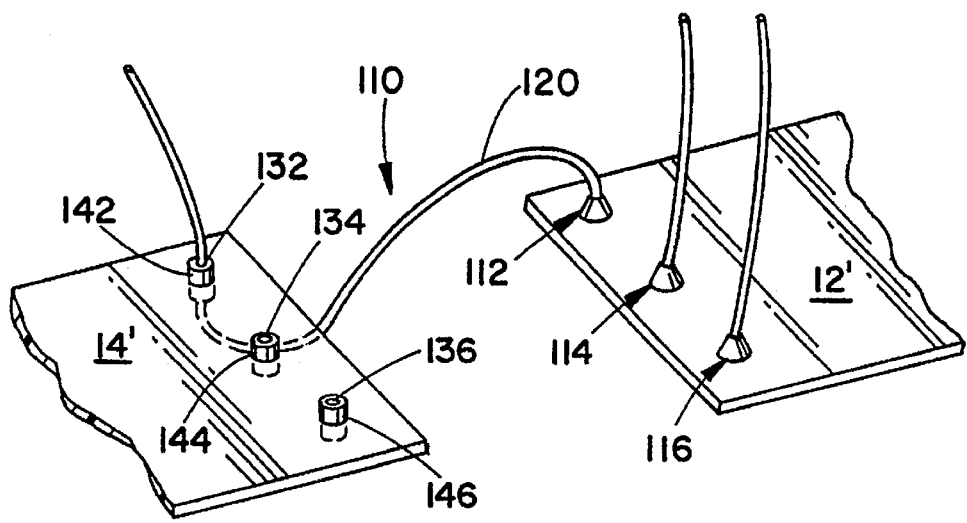
Figure 8B:
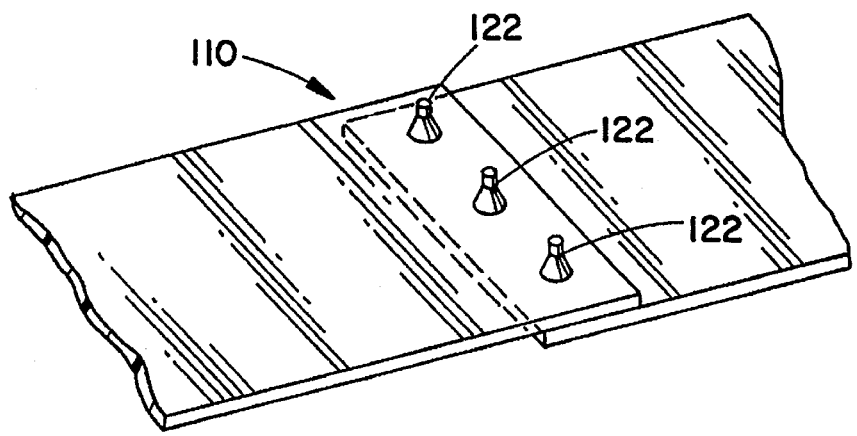
Figure 8C:
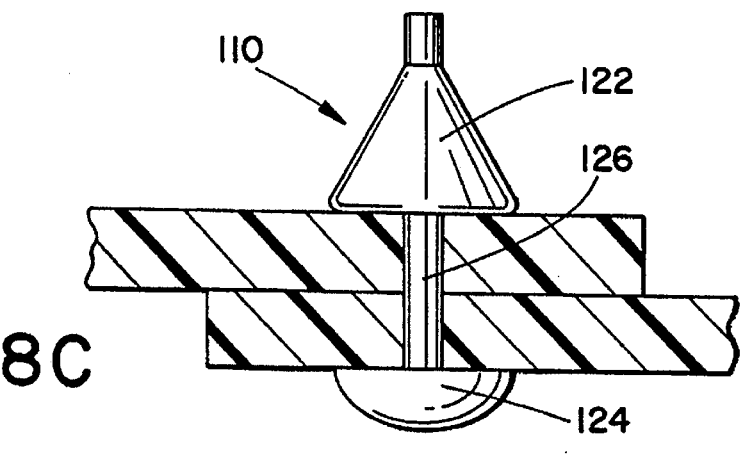

FIGS. 8a-8c best illustrate the rivet connector 110 according to an alternative preferred connector embodiment. The first end 12' of the sheet A' includes a plurality of specialized rivets 112, 114, and 116. Each of the rivets are preferably substantially identical to one another and accordingly, only a first specialized rivet 112 will be described in detail. The rivet 112 includes an elongate tail portion 120, a shoulder area 122, a head 124 and a connecting member 126 joining the shoulder area 122 to the head 124. The second end 14' of the sheet A' includes a plurality of apertures 132, 134 and 136 corresponding respectively to each of the specialized rivets 112, 114 and 116 disposed on the first end 12'. Each of the plurality of apertures 132, 134, and 136 are provided with annular guide members 142, 144 and 146 which are used as an aide to guide the elongate tail portions 120 through the apertures 132-136 provided in the first end 14'. Preferably, the plurality of rivets are made from a resilient rubberized biocompatible material whereby the shoulder area 122 is compressible in order to be pulled through the apertures 132-136 defined in the second end 14'. In use, the elongate tail portion 120 is guided through the aperture and guide member 132, 142 respectively whereupon the first end 12' is drawn adjacent and into contact with the second end 14'. The shoulder area 122 is pulled through the annular guide member 142 which is then removed. Lastly, the elongate tail portion 120 is cut from the rivet leaving only the shoulder area 122, the head 124, and the connecting member 126 in place. The first and second ends 12', 14' are thereby joined together by the cooperative forces between the shoulder area and head 122, 124 through the connecting member 126.

FIG. 5 illustrates the corrugated nerve cuff of the second embodiment in its final, relaxed state applied on a nerve. As with the first embodiment, the method of using the instant embodiment inserts electrodes into the nerve interfascicularly without penetration of perineurium membrane. The series of vee folds G are gently and slowly migrated into the nerve gradually over a period of time long enough to minimize the pressure on the nerve. Typically, the time period required for the cuff to function properly extends from about one (1) hour to several days depending upon specific application and situation. The driving force which motivates the conductive members B' inward is provided by the mechanical spring action of the plurality of sharp creases F formed in the conductive sheet A'.

A third preferred embodiment of the corrugated interfascicular nerve cuff is illustrated in FIG. 6 in an initial stretched state applied on a nerve. The cuff includes a corrugated non-conductive biocompatible resilient sheet A" which is molded to form a plurality of alternate peaks H and valleys I. In addition, the resilient sheet A" defines a plurality of longitudinally extending fin members J which are disposed on the sheet substantially in correspondence with alternate ones of the peaks H. A plurality of conductive segments B" are attached or embedded in the fin members J, the peaks and valleys I. The segments B" are preferably electrically conductive but may also be chemically, or otherwise fluid conductive or any combination of electrical, chemical or fluid conductive. The plurality of longitudinally extending fin members J are preferably disposed substantially in parallel to the first and second ends 12", 14" of the cuff. Further, the fin members J are preferably evenly distributed over the entire corrugated sheet A". However, it is to be understood that alterations to the illustrated cuff are possibly including the modification of limiting the number of fin members to a single fin member. Also, the longitudinal orientation of the corrugations and fin members may be altered to be slightly askew from parallel with the first and second ends 12", 14". More particularly, it is contemplated within the scope of the instant invention to provide a cuff having spiral or helical corrugations or fin members J or combined spiral, helical and longitudinal fin members.

The invention has been described with reference to the preferred embodiments. Obviously, modifications and alterations will occur to others upon a reading and understanding of this specification. It is intended to include all such modifications and alterations insofar as they come within the scope of the appended claims or the equivalents thereof.

Having thus described the invention, we now claim:

1. A nerve cuff apparatus comprising:
    a substantially non-conductive cylindrical body portion adapted to encircle a nerve and including at least one corrugation; and,
    at least one conductive segment disposed on said at least one corrugation of said body portion, capable of applying or recording electrical impulses.

2. The nerve cuff apparatus according to claim 1 wherein said cylindrical body portion is resiliently circumferentially expandable and contractible.

3. The nerve cuff apparatus according to claim 1 wherein said cylindrical body portion includes a plurality of corrugations.

4. The nerve cuff apparatus according to claim 3 further comprising a plurality of conductive segments disposed on said plurality of corrugations.

5. The nerve cuff apparatus according to claim 3 wherein at least a first one of said plurality of corrugations is adapted to pierce an epineurium membrane of an operatively associated nerve while avoiding piercing a perineurium membrane of the operatively associated nerve.

6. The nerve cuff apparatus according to claim 5 wherein said at least one conductive segment is disposed on said first one of said plurality of corrugations.

7. The nerve cuff apparatus according to claim 3 wherein said plurality of corrugations are adapted to pierce an epineurium membrane of an operatively associated nerve while avoiding piercing an perineurium membrane of the operatively associated nerve.

8. The nerve cuff apparatus according to claim 7 further comprising a plurality of conductive segments disposed on a first set of said plurality of corrugations.

9. The nerve cuff apparatus according to claim 8 wherein said substantially cylindrical body portion defines a central longitudinal axis and said plurality of corrugations are disposed on the body portion substantially in parallel with said longitudinal axis.

10. The nerve cuff apparatus according to claim 9 wherein said plurality of corrugations comprise a plurality of piercing members radially inwardly extending toward said central longitudinal axis.

11. The nerve cuff apparatus according to claim 10 wherein said plurality of conductive segments are disposed on said plurality of piercing members.

12. The nerve cuff apparatus according to claim 3 wherein at least a first one of said plurality of corrugations is adapted to penetrate a surface layer of body tissue.

13. The nerve cuff apparatus according to claim 3 wherein selected portions of said cylindrical body portion are configured to be in contact with an area including said nerve, thereby minimizing the contact between said area and said cylindrical body portion.

14. The nerve cuff apparatus according to claim 1 wherein said at least one conductive segment is electrically conductive.

15. The nerve cuff apparatus according to claim 1 wherein said substantially cylindrical body portion includes:
    a longitudinal slit defining opposing ends of the apparatus; and,
    a fastening member for connecting the opposing ends.

16. The nerve cuff apparatus according to claim 15 wherein said fastening member comprises a resilient member on a first opposing end adapted to extend through an aperture on the second opposing end for connecting said opposing ends in an overlapping relationship.

17. The nerve cuff apparatus according to claim 15 wherein said fastening member comprises:
    means defining an aperture in a first one of said opposing ends; and,
    a barbed member disposed on a second of said opposing ends, the barbed member adapted to extend through and hook the aperture for connecting said opposing ends in an overlapping relationship.

18. A method of installing a cylindrical cuff device onto an elongate nerve comprising the steps of:
    providing, as the cylindrical cuff device, a substantially planar sheet of a non-conductive material having at least one corrugation;
    encircling a nerve with the cylindrical cuff device; and,
    piercing an epineurium membrane of said nerve with said cylindrical cuff device while simultaneously circumferentially contracting said cylindrical cuff device.

19. The method according to claim 18 wherein the step of piercing includes urging a first member on the cuff device through said epineurium membrane while avoiding piercing a perineurium membrane of said nerve.

20. The method according to claim 18 wherein the step of piercing includes piercing said epineurium membrane by circumferentially contracting said planar sheet.

21. The method according to claim 18 wherein the step of piercing includes urging a plurality of first members on the cuff device through said epineurium membrane and avoiding piercing a perineurium membrane of said nerve.

22. A nerve cuff apparatus comprising:

a substantially cylindrical corrugated body member adapted to encircle a nerve; and, at least one conductive segment disposed on a corrugated segment of said corrugated body member, capable of applying or recording electrical impulses.

23. The nerve cuff apparatus according to claim 22 wherein said body member is resiliently circumferentially expandable and contractible.

24. The nerve cuff apparatus according to claim 22 wherein said cylindrical body member includes a plurality of corrugations.

25. The nerve cuff apparatus according to claim 24 further comprising a plurality of conductive segments disposed on said body member.

26. The nerve cuff apparatus according to claim 25 wherein said plurality of conductive segments are disposed on said plurality of corrugations.

27. The nerve cuff apparatus according to claim 24 wherein at least a first one of said plurality of corrugations is adapted to pierce a epineurium membrane of an operatively associated nerve while avoiding piercing a perineurium membrane of the operatively associated nerve.

28. The nerve cuff apparatus according to claim 27 wherein said at least one conductive segment is disposed on said first one of said plurality of corrugations.

29. The nerve cuff apparatus according to claim 24 wherein said plurality of corrugations are adapted to pierce an epineurium membrane of an operatively associated nerve while avoiding piercing an perineurium membrane of the operatively associated nerve.

30. The nerve cuff apparatus according to claim 29 further comprising a plurality of conductive segments disposed on a first set of said plurality of corrugations.

31. The nerve cuff apparatus according to claim 30 wherein said substantially cylindrical corrugated body member defines a central longitudinal axis and said plurality of corrugations are disposed on the body member substantially in parallel with said longitudinal axis.

32. The nerve cuff apparatus according to claim 31 wherein said plurality of corrugations comprise a plurality of piercing members radially inwardly extending toward said central longitudinal axis.

33. The nerve cuff apparatus according to claim 32 wherein said plurality of conductive segments are disposed on said plurality of piercing members.

34. The nerve cuff apparatus according to claim 22 wherein said at least one conductive segment is electrically conductive.

35. The nerve cuff apparatus according to claim 22 wherein said substantially cylindrical body member includes:

a longitudinal slit defining opposing ends of the apparatus; and, a fastening member for connecting the opposing ends.

36. The nerve cuff apparatus according to claim 35 wherein said fastening member comprises a resilient member on a first opposing end adapted to extend through an aperture on the second opposing end for connecting said opposing ends in an overlapping relationship.

37. The nerve cuff apparatus according to claim 22 further including, a fastening member comprising:

means defining an aperture in a first one of opposing ends of said body member; and, a barbed member disposed on a second of said opposing ends of said body member, the barbed member adapted to extend through and hook the aperture for connecting said opposing ends in an overlapping relationship.

* * * * *

UNITED STATES PATENT AND TRADEMARK OFFICE
CERTIFICATE OF CORRECTION

PATENT NO. : 5,634,462
DATED      : June 3, 1997
INVENTOR(S): Dustin J. Tyler et al.

It is certified that error appears in the above-identified patent and that said Letters Patent is hereby corrected as shown below:

Column 1, before "Background of the Invention", please insert the following paragraph:

---This invention was made with government support under Grant No. NIH NS32845 awarded by the National Institutes of Health. The government has certain rights in this invention.---

Signed and Sealed this

Twenty-ninth Day of June, 1999

Attest:

Q. TODD DICKINSON

*Attesting Officer*    Acting Commissioner of Patents and Trademarks